US009359416B2

(12) United States Patent
Kiyokawa et al.

(10) Patent No.: US 9,359,416 B2
(45) Date of Patent: Jun. 7, 2016

(54) DNA ENCODING CANINE MONOMERIC CRP AND EXPRESSION VECTOR CONTAINING THE DNA

(71) Applicants: NITTO BOSEKI CO., LTD., Fukushima-shi, Fukushima (JP); NATIONAL INSTITUTE OF AGROBIOLOGICAL SCIENCES, Tsukuba-shi, Ibaraki (JP)

(72) Inventors: Iwao Kiyokawa, Koriyama (JP); Yuji Arimatsu, Koriyama (JP); Toshihide Miura, Koriyama (JP); Ryo Kojima, Koriyama (JP); Hideki Sezutsu, Tsukuba (JP); Keiro Uchino, Tsukuba (JP); Isao Kobayashi, Tsukuba (JP); Toshiki Tamura, Tsukuba (JP)

(73) Assignees: NITTO BOSEKI CO., LTD., Fukushima-shi (JP); NATIONAL INSTITUTE OF AGROBIOLOGICAL SCIENCES, Tsukuba-shi (JP)

( * ) Notice: Subject to any disclaimer, the term of this patent is extended or adjusted under 35 U.S.C. 154(b) by 64 days.

(21) Appl. No.: 14/487,513

(22) Filed: Sep. 16, 2014

(65) Prior Publication Data
US 2015/0037880 A1 Feb. 5, 2015

Related U.S. Application Data

(62) Division of application No. 13/701,946, filed as application No. PCT/JP2011/062343 on May 30, 2011, now Pat. No. 8,865,966.

(30) Foreign Application Priority Data

Jun. 11, 2010 (JP) ................................ 2010-133601

(51) Int. Cl.
 *C07K 14/47* (2006.01)
 *A01K 67/033* (2006.01)
 *A01K 67/04* (2006.01)

(52) U.S. Cl.
 CPC ......... *C07K 14/4737* (2013.01); *A01K 67/0333* (2013.01); *A01K 67/04* (2013.01); *A01K 2217/052* (2013.01); *A01K 2227/706* (2013.01); *C07K 2319/02* (2013.01)

(58) Field of Classification Search
 CPC .................................................. C07K 14/4737
 USPC ...................................................... 514/44 R
 See application file for complete search history.

(56) References Cited

U.S. PATENT DOCUMENTS

| 5,702,921 A | 12/1997 | Tanaka |
| 7,459,599 B2 | 12/2008 | Tamura et al. |
| 2011/0021757 A1 | 1/2011 | Tamura et al. |

FOREIGN PATENT DOCUMENTS

| CN | 101331228 A | 12/2008 |
| EP | 0 622 460 A2 | 11/1994 |
| JP | 2000-014388 | 1/2000 |
| JP | 2006-137739 A | 6/2006 |
| WO | 2007/046439 A1 | 4/2007 |

OTHER PUBLICATIONS

Morikazu Imamura, et al.; Targeted Gene Expression Using the GAL4/UAS System in the Silkworm *Bombyx mori.*; Genetics 165: 1329-1340 (Nov. 2003).
PCT Notification of Transmittal of Translation of the International Preliminary Report on Patentability dated Jan. 24, 2013, regarding International Application No. PCT/JP2011/062343.
Yoon, Sung Ho, et al., "Secretory Production of Recombinant Proteins in *Escherichia coli*," Recent Patents on Biotechnology (2010) No. 4, pp. 23-29.
Fischer, Janice A., et al., "GAL4 activates transcription in *Drosophila*," Nature, vol. 332 (1988), pp. 853-856.
Brand, Andrea H., et al., "Targeted gene expression as a means of altering cell fates and generating dominant phenotypes," Development, No. 118 (1993) pp. 401-415.
Toshiki, Tamura, et al., "Germline transformation of the silkworm *Bombyx mori* L. Using a *piggyBac* transposon-derived vector," Nature Biotechnology, vol. 18 (2000), pp. 81-84.
Kishimoto, Michiyuki, et al., "Cloning of Canine C-reactive Protein (CRP) and expression of recombinant protein thereof," Japanese Society of Veterinary Science Gakajutsu Shukai Koen Yoshishu (2009), pp. 284, I-34, with English translation.
Lindblad-Toh, Kerstin, et al., "Genome sequence, comparative analysis and haplotype structure of the domestic dog," Nature, vol. 438 (2005), pp. 803-819.
Rassouli, Mohammad, et al., "Derivation of the amino Acid Sequnce of Rat C-reactive Protein from cDNA Cloning with Additional Studies on the Nature of Its Dimeric Component," The Journal of Biological Chemistry, vol. 167, No. 5 (1992), pp. 2947-2954.
GenBank AB005545.1, "Sus scrofa mRNA for C-reactive protein, complete cds," Aug. 16, 2011, www.ncbi.nlm.nih.gov/nuccore/AB005545.
Chinese Office Action dated Sep. 26, 2013, in the corresponding Chinese patent application No. 201180033762.
NCBI Reference Sequence: XP_545746.2, "Predicted: similar to C-reactive protein precursor [Canis familiaris] Protein," Oct. 17, 2013, www.ncbi.nlm.nih.gov/protein/XP_545746.2.
Supplementary European Search Report dated Nov. 7, 2013, in the corresponding European patent application No. 11792315.1.
Tanaka, Toshio, et al., "Secretory production of recombinant human C-reactive protein in *Escherichia coli*, capable of binding with phosphorylcholine, and its characterization," Biochemical and Biophysical Research Communication, vol. 295 (2002), pp. 163-166.
Hirschfield, Gideon M., et al., "Transgenic human C-reactive protein is not proatherogenic in apolipoprotein E-deficient mice," PNAS, vol. 102, No. 23 (2005), pp. 8309-8314.
Pepys, Mark B., et al., "Proinflammatory Effects of Bacterial Recombinant Human C-Reactive Protein are Caused by Contamination With Bacterial Products, Not by C-Reactive Protein Itself," Circulation Research 97 (2005), pp. e97-e103, plus cover page.

(Continued)

*Primary Examiner* — Anoop Singh
*Assistant Examiner* — David A Montanari
(74) *Attorney, Agent, or Firm* — Kratz, Quintos & Hanson, LLP

(57) ABSTRACT

Pentameric CRP is produced at a high efficiency by transferring DNA, which encodes monomeric CRP, into a silkworm to thereby construct a transgenic silkworm and then collecting and purifying pentameric CRP that is produced by the transgenic silkworm constructed above.

6 Claims, 3 Drawing Sheets

(56) References Cited

OTHER PUBLICATIONS

Tatematsu, Ken-ichiro, et al., "Construction of a binary transgenic gene expression system for recombinant protein production in the middle silk gland of the silkworm *Bombyx mori*," Transgenic Res, vol. 19 (2010) pp. 473-487.
Database UniProt [On line] "Uncharacterized protein from dog (*Canis lupus* familiaris)," XP002715215, Nov. 30, 2010, retrieved from EBI accession No. UniProt:E2R5J0.
Chinese Office Action dated May 7, 2014, in the corresponding Chinese patent application No. 201180033762.6.
Wang, Chang-he, et al., "Research Advances and Developing Prospect of Bombyx mori Bioreactor," Sichuan Journal of Zoology, vol. 23, No. 4 (2004), pp. 368-373, with English abstract.
Wei, Ke-qiang, et al., "Research on the production of genetic vaccines using silkworm (*Bombyx mori*) as bioreactor," Chinese Journal of Veterinary Drug, vol. 38, No. 5 (2004), pp. 35-37, with English abstract.
Koike et al. (2009, Circulation, vol. 120, pp. 2088-2094).
Kato et al. (e-published Oct. 15, 2009, Appl. Microbiol. Biotechnol., vol. 85, pp. 459-470).
Eisenhardt et al. (2009, Circ. Res. vol. 105, pp. 128-137).
Woo et al. (1985, JBC vol. 260(24), pp. 13384-13388).
Xia et al. (1997, PNAS, vol. 94, pp. 2575-2580).
Communication under 114(2) EPC mailed on Feb. 10, 2016 in corresponding EP application No. 11792315.1.
Communication under 114(2) EPC mailed on Feb. 11, 2016 in corresponding EP application No. 11792315.1.
Caspi et al., "Isolation and characterization of C-reactive protein from the dog", Immunology (May 1984), 53:307-313.
Lei et al., Genomic DNA Sequence for Human C-reactive Protein, J Biol. Chem. (Mar. 26, 1985), 260 (24):13377-13383.
Whitehead et al., "Mouse C-reactive protein", Biochem. J (1990), 266:283-290.
Yamamoto et al., "Isolation of canine C-reactive protein and characterization of its properties", Vet Immunol Imunopathol. (1992), 30(4):329-339.
Marnell et al "Epression and Radiolabeling of Human C-Reactive Protein in Baculovius-Infected Cell Lines and Trichoplusia ni Larvae", Protein Expr Purif. (1995), 6(4):439-446.
NCBI Reference Sequence XP_545746.1.
NCBI Reference Sequence XM_545746.1.
NCBI Reference Sequence XP_545746.2.
NCBI Reference Sequence XM_545746.2.
NCBI Reference Sequence XP_545746.3
NCBI Reference Sequence XM_545746.3.
NCBI Reference Sequence XP_545746.4.
NCBI Reference Sequence XM_545746.4.
NCBI Reference Sequence NP_000558.2
UniProtKB—P48199.
UniProtKB—O19062.
UniProtKB—P14847.
ICL, "Dog CRP ELISA Kit", <http://www.icllab.com/dog-crp-elisa-kit.html>.

SEQUENCE LISTING

```
<160> NUMBER OF SEQ ID NOS: 10

<210> SEQ ID NO 1
<211> LENGTH: 202
<212> TYPE: PRT
<213> ORGANISM: Canis familiaris

<400> SEQUENCE: 1

Asp Leu Asp Glu Lys Ala Phe Val Phe Pro Arg Glu Ser Glu Asn Ser
1               5                   10                  15

Tyr Val Ile Leu Phe Pro Gln Leu Gln Lys Pro Met Lys Ala Phe Thr
            20                  25                  30
```

```
Val Cys Leu Gln Val Tyr Thr Asp Leu Thr Arg Pro His Ser Leu Phe
            35                  40                  45

Ser Tyr Ala Thr Lys Ser Gln Ser Asn Glu Ile Leu Leu Phe Lys Glu
 50                      55                  60

Arg Pro Gly Leu Phe Ser Val Ser Val Gly Gly Ser Asp Ala Phe Ile
 65                  70                  75                  80

Asn Phe Pro Gln Lys Phe Tyr Ala Pro Gln His Phe Cys Val Thr Trp
                 85                  90                  95

Glu Ser Val Thr Gly Leu Thr Glu Leu Trp Val Asp Gly Lys Pro Met
            100                 105                 110

Val Arg Ala Ser Leu Arg Arg Gly Tyr Thr Val Gly Ser Gly Ala Ser
        115                 120                 125

Ile Val Leu Gly Gln Glu Gln Asp Ser Phe Gly Gly Phe Asp Lys
    130                 135                 140

Asn Gln Ser Leu Val Gly Asp Ile Glu Asp Val Asn Met Trp Asp Phe
145                 150                 155                 160

Val Leu Ser Pro Ser Gln Ile Leu Thr Leu Tyr Thr Thr Arg Ala Leu
                165                 170                 175

Ser Pro Asn Val Leu Asn Trp Arg Asn Leu Arg Tyr Glu Thr Arg Gly
            180                 185                 190

Glu Val Phe Leu Lys Lys Glu Leu Trp Ser
        195                 200

<210> SEQ ID NO 2
<211> LENGTH: 19
<212> TYPE: PRT
<213> ORGANISM: Canis familiaris

<400> SEQUENCE: 2

Met Glu Lys Leu Trp Pro Cys Leu Leu Val Leu Met Asn Leu Pro Ser
  1               5                  10                  15

Ala Ser Arg

<210> SEQ ID NO 3
<211> LENGTH: 221
<212> TYPE: PRT
<213> ORGANISM: Canis familiaris

<400> SEQUENCE: 3

Met Glu Lys Leu Trp Pro Cys Leu Leu Val Leu Met Asn Leu Pro Ser
  1               5                  10                  15

Ala Ser Arg Asp Leu Asp Glu Lys Ala Phe Val Phe Pro Arg Glu Ser
             20                  25                  30

Glu Asn Ser Tyr Val Ile Leu Phe Pro Gln Leu Gln Lys Pro Met Lys
             35                  40                  45

Ala Phe Thr Val Cys Leu Gln Val Tyr Thr Asp Leu Thr Arg Pro His
 50                  55                  60

Ser Leu Phe Ser Tyr Ala Thr Lys Ser Gln Ser Asn Glu Ile Leu Leu
 65                  70                  75                  80

Phe Lys Glu Arg Pro Gly Leu Phe Ser Val Ser Val Gly Gly Ser Asp
                 85                  90                  95

Ala Phe Ile Asn Phe Pro Gln Lys Phe Tyr Ala Pro Gln His Phe Cys
            100                 105                 110

Val Thr Trp Glu Ser Val Thr Gly Leu Thr Glu Leu Trp Val Asp Gly
        115                 120                 125

Lys Pro Met Val Arg Ala Ser Leu Arg Arg Gly Tyr Thr Val Gly Ser
```

| | | | | | | | | | | |
|---|---|---|---|---|---|---|---|---|---|---|
| | | 130 | | | 135 | | | 140 | | |
| Gly | Ala | Ser | Ile | Val | Leu | Gly | Gln | Glu | Gln | Asp | Ser | Phe | Gly | Gly |
| 145 | | | | 150 | | | | 155 | | | | 160 |

Gly Ala Ser Ile Val Leu Gly Gln Glu Gln Asp Ser Phe Gly Gly
145                 150                 155                 160

Phe Asp Lys Asn Gln Ser Leu Val Gly Asp Ile Glu Asp Val Asn Met
                165                 170                 175

Trp Asp Phe Val Leu Ser Pro Ser Gln Ile Leu Thr Leu Tyr Thr Thr
            180                 185                 190

Arg Ala Leu Ser Pro Asn Val Leu Asn Trp Arg Asn Leu Arg Tyr Glu
        195                 200                 205

Thr Arg Gly Glu Val Phe Leu Lys Lys Glu Leu Trp Ser
210                 215                 220

<210> SEQ ID NO 4
<211> LENGTH: 606
<212> TYPE: DNA
<213> ORGANISM: Canis familiaris

<400> SEQUENCE: 4

```
gacctggacg agaaagcctt cgttttccct agagaatcgg aaaactccta cgtcatcctg      60
ttcccacaat tacagaagcc aatgaaagct ttcacagtct gcttgcaagt gtacacggac     120
ctgacccgtc cgcatagttt attcagctac gctactaaat ctcaaagcaa cgaaatattg     180
ctgttcaaag aacgcccagg cttattcagc gtctcagttg gcggatcaga tgccttcatt     240
aacttccccc aaaaattcta cgctccccag catttctgcg ttacatggga atcggtcacc     300
ggtctgactg agttatgggt cgacggaaaa cctatggtta gcttcattg agaagaggc      360
tacacggttg gttctggtgc cagcattgtt ctgggtcaag aacaggactc cttcggagga     420
ggcttcgata aaaatcaatc actcgtggga gatatagaag acgtgaacat gtgggacttc     480
gtgttaagtc caagtcaaat cctgacatta tacactacca gagctctcag ccctaacgtg     540
ttgaattgga gaaacctgag atacgaaaca gaggtgaagt cttcctgaa aaagaattg       600
tggtct                                                                606
```

<210> SEQ ID NO 5
<211> LENGTH: 57
<212> TYPE: DNA
<213> ORGANISM: Canis familiaris

<400> SEQUENCE: 5

```
atggagaagc tgtggccttg tctcctggtc ctcatgaacc tcccttctgc ttcccgt         57
```

<210> SEQ ID NO 6
<211> LENGTH: 663
<212> TYPE: DNA
<213> ORGANISM: Canis familiaris

<400> SEQUENCE: 6

```
atggagaagc tgtggccttg tctcctggtc ctcatgaacc tcccttctgc ttcccgtgac      60
ctggacgaga agccttcgt tttccctaga gaatcggaaa actcctacgt catcctgttc     120
ccacaattac agaagccaat gaaagctttc acagtctgct tgcaagtgta cacggacctg     180
acccgtccgc atagtttatt cagctacgct actaaatctc aaagcaacga atattgctg      240
ttcaaagaac gcccaggctt attcagcgtc tcagttggcg gatcagatgc cttcattaac     300
ttcccccaaa aattctacgc tccccagcat ttctgcgtta catgggaatc ggtcaccggt     360
ctgactgagt tatgggtcga cggaaaacct atggttagag cttcattgag aagaggctac     420
```

```
acggttggtt ctggtgccag cattgttctg ggtcaagaac aggactcctt cggaggaggc    480
ttcgataaaa atcaatcact cgtgggagat atagaagacg tgaacatgtg ggacttcgtg    540
ttaagtccaa gtcaaatcct gacattatac actaccagag ctctcagccc taacgtgttg    600
aattggagaa acctgagata cgaaacaaga ggtgaagtct tcctgaaaaa agaattgtgg    660
tct                                                                  663
```

<210> SEQ ID NO 7
<211> LENGTH: 206
<212> TYPE: PRT
<213> ORGANISM: Homo sapiens

<400> SEQUENCE: 7

```
Gln Thr Asp Met Ser Arg Lys Ala Phe Val Phe Pro Lys Glu Ser Asp
 1               5                  10                  15

Thr Ser Tyr Val Ser Leu Lys Ala Pro Leu Thr Lys Pro Leu Lys Ala
            20                  25                  30

Phe Thr Val Cys Leu His Phe Tyr Thr Glu Leu Ser Ser Thr Arg Gly
        35                  40                  45

Tyr Ser Ile Phe Ser Tyr Ala Thr Lys Arg Gln Asp Asn Glu Ile Leu
    50                  55                  60

Ile Phe Trp Ser Lys Asp Ile Gly Tyr Ser Phe Thr Val Gly Gly Ser
65                  70                  75                  80

Glu Ile Leu Phe Glu Val Pro Glu Val Thr Val Ala Pro Val His Ile
                85                  90                  95

Cys Thr Ser Trp Glu Ser Ala Ser Gly Ile Val Glu Phe Trp Val Asp
            100                 105                 110

Gly Lys Pro Arg Val Arg Lys Ser Leu Lys Lys Gly Tyr Thr Val Gly
        115                 120                 125

Ala Glu Ala Ser Ile Ile Leu Gly Gln Glu Gln Asp Ser Phe Gly Gly
    130                 135                 140

Asn Phe Glu Gly Ser Gln Ser Leu Val Gly Asp Ile Gly Asn Val Asn
145                 150                 155                 160

Met Trp Asp Phe Val Leu Ser Pro Asp Glu Ile Asn Thr Ile Tyr Leu
                165                 170                 175

Gly Gly Pro Phe Ser Pro Asn Val Leu Asn Trp Arg Ala Leu Lys Tyr
            180                 185                 190

Glu Val Gln Gly Glu Val Phe Thr Lys Pro Gln Leu Trp Pro
        195                 200                 205
```

<210> SEQ ID NO 8
<211> LENGTH: 18
<212> TYPE: PRT
<213> ORGANISM: Homo sapiens

<400> SEQUENCE: 8

```
Met Glu Lys Leu Leu Cys Phe Leu Val Leu Thr Ser Leu Ser His Ala
 1               5                  10                  15

Phe Gly
```

<210> SEQ ID NO 9
<211> LENGTH: 618
<212> TYPE: DNA
<213> ORGANISM: Homo sapiens

<400> SEQUENCE: 9

```
cagacagaca tgtcgaggaa ggcttttgtg tttcccaaag agtcggatac ttcctatgta     60
```

```
tccctcaaag caccgttaac gaagcctctc aaagccttca ctgtgtgcct ccacttctac    120
acggaactgt cctcgacccg tgggtacagt attttctcgt atgccaccaa gagacaagac    180
aatgagattc tcatattttg gtctaaggat ataggataca gttttacagt gggtgggtct    240
gaaatattat tcgaggttcc tgaagtcaca gtagctccag tacacatttg tacaagctgg    300
gagtccgcct cagggatcgt ggagttctgg gtagatggga agcccagggt gaggaagagt    360
ctgaagaagg gatacactgt gggggcagaa gcaagcatca tcttgggggca ggagcaggat    420 tccttcggtg ggaactttga aggaagccag tccctggtgg gagacattgg aaatgtgaac    480
atgtgggact ttgtgctgtc accagatgag attaacacca tctatcttgg cgggcccttc    540
agtcctaatg tcctgaactg gcgggcactg aagtatgaag tgcaaggcga agtgttcacc    600 aaacccagc tgtggccc                                                   618

<210> SEQ ID NO 10
<211> LENGTH: 54
<212> TYPE: DNA
<213> ORGANISM: Homo sapiens

<400> SEQUENCE: 10
atggagaagc tgttgtgttt cttggtcttg accagcctct ctcatgcttt tggc          54
```

DNA ENCODING CANINE MONOMERIC CRP AND EXPRESSION VECTOR CONTAINING THE DNA

TECHNICAL FIELD

The present invention relates to a method for producing a pentameric C-reactive protein (CRP) using a silkworm. The present invention also relates to a transgenic silkworm producing pentameric CRP and a method for producing the same. The present invention further relates to a DNA encoding monomeric canine CRP and an expression vector comprising the DNA.

BACKGROUND ART

CRP is a protein that is active in the form of pentameric CRP composed of five CRP monomers via noncovalent bonds. Most of CRPs are found as pentameric CRPs in vivo. In the present specification, CRP means pentameric CRP unless otherwise specified.

In the field of clinical study, CRP is one type of acute-phase protein that is increased due to acute inflammation or acute breakdown of tissue, and is known as a typical inflammation marker. The quantification of CRP is indispensable for observing the activities, severities, or courses of various diseases responsible for inflammation or tissue damage. Thus, CRP is routinely assayed in hospitals, clinical study centers, or the like. CRP assay kits used in this procedure often contain standard CRP solutions. Thus, CRP is consumed in large amounts every day. For such reasons, the production of highly pure and inexpensive CRP has been demanded.

Studies have been made on use of genetic engineering approaches for producing highly pure CRP. Only a genetic engineering method for producing CRP with *E. coli* as a host (Patent Literature 1) has been achieved commercially.

CITATION LIST

Patent Literature

Patent Literature 1: U.S. Pat. No. 5,702,921

SUMMARY OF INVENTION

Technical Problem

The production of highly pure and ever more inexpensive CRP using a genetic engineering approach requires improving the CRP production efficiency of a host and reducing cost necessary for the collection of CRP produced by the host. Hosts more suitable for CRP production than conventional hosts must be searched for in order to attain these purposes.

Specifically, the method for producing CRP with *E. coli* as a host disclosed in Patent Literature 1 involves allowing the bacterium to secrete ex vivo, by the action of kil gene, CRP, which originally accumulates in the periplasm region. The secretion of CRP into a medium is intended to facilitate CRP purification and reduce cost necessary for CRP collection. Unfortunately, bacterial strains overexpressing the kit genes are generally unsuitable for high-density culture (Poon, S. H. et al., Recent Pat. Biotechnol., 4, 23-29, 2010). From this regard, concentration and purification procedures for obtaining highly pure CRP are complicated and thus become an obstacle to further improvement in CRP production efficiency.

In consideration of this situation, an object of the present invention is to provide a novel method for producing pentameric CRP that can be produced with high efficiency, a transgenic silkworm suitable for such production of pentameric CRP, a method for producing the transgenic silkworm, a DNA encoding monomeric canine CRP, and an expression vector comprising the DNA.

Solution to Problem

The present inventors have conducted diligent studies aimed at attaining the object described above and consequently found that, surprisingly, a transgenic silkworm can express pentameric CRP formed via noncovalent bonds with its pentameric structure and activity maintained, and can secrete the pentameric CRP without coexpressing the kil gene or the like that promotes secretion; thus, pentameric CRP can be produced with high efficiency; and the produced pentameric CRP can be collected easily from the transgenic silkworm. Based on these findings, the present invention has been completed.

Thus, the present invention relates to a method for producing pentameric CRP, a transgenic silkworm producing pentameric CRP, a method for producing the transgenic silkworm, a DNA encoding monomeric canine CRP, and an expression vector comprising the DNA, shown in [1] to [25] below.

[1] A method for producing pentameric CRP, comprising: a preparation step of preparing a transgenic silkworm containing a monomeric CRP-encoding DNA; and a collection step of collecting pentameric CRP produced by the prepared transgenic silkworm.

[2] The production method according to [1], wherein the preparation step is the step of preparing a transgenic silkworm containing a transcription factor-encoding DNA operably linked downstream of a promoter of a DNA encoding a protein specifically expressed in a silk gland, and a monomeric CRP-encoding DNA operably linked downstream of a target promoter of the transcription factor.

[3] The production method according to [1], wherein the preparation step is the step of preparing a transgenic silkworm by mating a silkworm containing a transcription factor-encoding DNA operably linked downstream of a promoter of a DNA encoding a protein specifically expressed in a silk gland, and a silkworm containing a monomeric CRP-encoding DNA operably linked downstream of a target promoter of the transcription factor.

[4] The production method according to [2] or [3], wherein the transcription factor is GAL4, and the target promoter is UAS.

[5] The production method according to any of [2] to [4], wherein the collection step is the step of collecting pentameric CRP produced by the prepared transgenic silkworm into its silk gland.

[6] The production method according to any of [1] to [5], wherein the CRP is canine CRP.

[7] The production method according to any of [1] to [6], wherein the monomeric CRP-encoding DNA is a DNA encoding an amino acid sequence comprising a sequence represented by SEQ ID NO: 1.

[8] The production method according to any of [1] to [7], wherein the monomeric CRP-encoding DNA is a DNA comprising a nucleotide sequence represented by SEQ ID NO: 4.

[9] A transgenic silkworm containing a monomeric CRP-encoding DNA and producing pentameric CRP.

[10] A transgenic silkworm containing a transcription factor-encoding DNA operably linked downstream of a promoter of a DNA encoding a protein specifically expressed in a silk gland, and a monomeric CRP-encoding DNA operably linked downstream of a target promoter of the transcription factor, and producing pentameric CRP into its silk gland.

[11] The transgenic silkworm according to [10], wherein the transcription factor is GAL4, and the target promoter is UAS.

[12] The transgenic silkworm according to any of [9] to [11], wherein the CRP is canine CRP.

[13] The transgenic silkworm according to any of [9] to [12], wherein the monomeric CRP-encoding DNA is a DNA encoding an amino acid sequence comprising a sequence represented by SEQ ID NO: 1.

[14] The transgenic silkworm according to any of [9] to [13], wherein the monomeric CRP-encoding DNA is a DNA comprising a nucleotide sequence represented by SEQ ID NO: 4.

[15] A method for producing a transgenic silkworm producing pentameric CRP, comprising an introduction step of introducing a monomeric CRP-encoding DNA into a silkworm.

[16] A method for producing a transgenic silkworm producing pentameric CRP into its silk gland, comprising an introduction step of introducing a transcription factor-encoding DNA operably linked downstream of a promoter of a DNA encoding a protein specifically expressed in a silk gland, and a monomeric CRP-encoding DNA operably linked downstream of a target promoter of the transcription factor into a silkworm.

[17] The production method according to [16], wherein the introduction step is the step of preparing a DNA-introduced silkworm by mating a silkworm containing a transcription factor-encoding DNA operably linked downstream of a promoter of a DNA encoding a protein specifically expressed in a silk gland, and a silkworm containing a monomeric CRP-encoding DNA operably linked downstream of a target promoter of the transcription factor.

[18] The production method according to [16] or [17], wherein the transcription factor is GAL4, and the target promoter is UAS.

[19] The production method according to any of [15] to [18], wherein the CRP is canine CRP.

[20] The production method according to any of [15] to [19], wherein the monomeric CRP-encoding DNA is a DNA encoding an amino acid sequence comprising a sequence represented by SEQ ID NO: 1.

[21] The production method according to any of [15] to [20], wherein the monomeric CRP-encoding DNA is a DNA comprising a nucleotide sequence represented by SEQ ID NO: 4.

[22] A DNA encoding monomeric canine CRP, the DNA comprising a nucleotide sequence encoding an amino acid sequence comprising a sequence represented by SEQ ID NO: 1.

[23] The DNA encoding monomeric canine CRP according to [22], wherein the nucleotide sequence is a nucleotide sequence comprising a sequence represented by SEQ ID NO: 4.

[24] An expression vector comprising a nucleotide sequence of a DNA encoding monomeric canine CRP according to [22] or [23].

[25] The expression vector according to [24], wherein the nucleotide sequence is operably linked downstream of UAS.

The pentameric CRP according to the present invention refers to a pentamer that is formed from five CRP monomers via noncovalent bonds and has activity in vivo. In this context, the phrase "having activity in vivo" preferably means that the pentameric CRP according to the present invention can function as in serum-derived CRP and be used as a calibrator for CRP assay kits used in the field of clinical study and as an antigen for CRP assay kits in preparing anti-CRP antibodies.

In the present invention, the phrase "operably linked downstream of a promoter" means that a DNA is linked to a promoter such that the expression of the DNA located downstream of the promoter is induced by the binding of a transcription factor to the promoter. In this context, a DNA may be bound with another gene and expressed as a fusion protein with another gene product. Even in such a case, it should be understood that the DNA is operably linked downstream of a promoter as long as the expression of this fusion protein is induced by the binding of a transcription factor to the promoter.

Advantageous Effects of Invention

The method of the present invention for producing pentameric CRP can produce, with high efficiency, pentameric CRP having activity equivalent to serum-derived CRP. Particularly, the method of the present invention for producing pentameric CRP facilitates the collection of pentameric CRP, because the resulting transgenic silkworm expresses and secretes the pentameric CRP. CRP produced by the method of the present invention for producing pentameric CRP is very useful as a calibrator for CRP assay kits used in the field of clinical study. Also, CRP produced according to the present invention can be used as an antigen for CRP assay kits in preparing anti-CRP antibodies.

DESCRIPTION OF EMBODIMENTS

Figure 1:
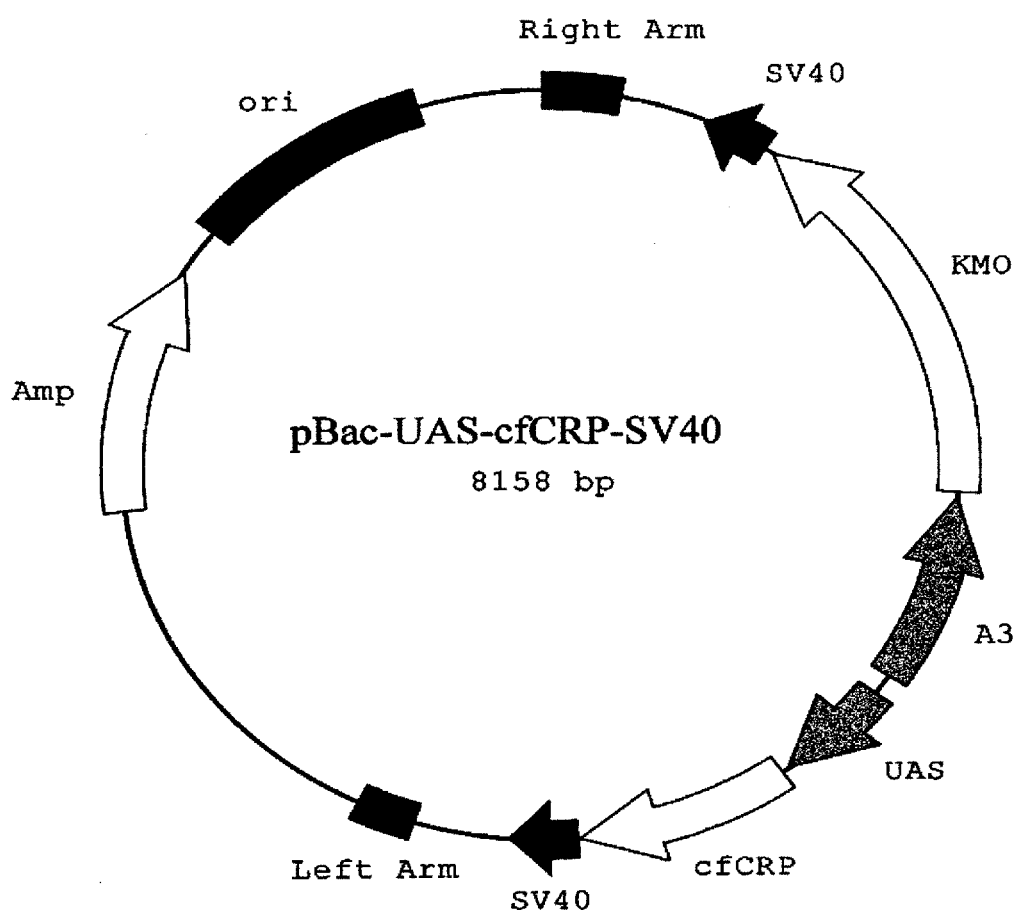
FIG. 1 is a diagram showing the structure of pBac-UAS-cfCRP-SV40.

Examples of CRP produced by the method of the present invention for producing pentameric CRP include CRPs derived from humans, dogs, mice, rats, rabbits, donkeys, goats, horses, pigs, birds, and cats. Among them, human-derived CRP or CRP derived from an ornamental animal such as a dog or a cat is preferable, and dog- or cat-derived CRP is more preferable, with dog-derived CRP particularly preferred. This is because human CRP is in high demand in the field of clinical study and because there is also a growing demand for ornamental animal-derived CRP such as canine CRP or feline CRP with recent progress in pet medicine. Particularly, CRP derived from the serum of an ornamental animal such as a dog or a cat is distributed only in small amounts and does not meet the growing demand under the present circumstances. Particularly, canine or feline CRP shows a very large imbalance of demand versus supply due to the popularity of these pets. Such a demand can be coped with by producing human CRP, canine CRP, feline CRP, or CRP derived from other ornamental animals with high efficiency by the method of the present invention for producing pentameric CRP. A genetic engineering production method has not yet been established, particularly, for canine CRP. In this regard, the method of the present invention for producing pentameric CRP is of great value, because it can produce canine CRP with high efficiency.

The monomeric CRP-encoding DNA commonly used in the present invention is a DNA encoding a monomer of the CRP produced by the method of the present invention for producing pentameric CRP. The monomeric CRP-encoding DNA is preferably a DNA encoding a human CRP or canine CRP monomer, more preferably a DNA encoding monomeric canine CRP.

In this context, examples of the DNA encoding monomeric canine CRP preferably include a DNA encoding an amino acid sequence comprising the sequence represented by SEQ ID NO: 1, more preferably a DNA comprising the nucleotide sequence represented by SEQ ID NO: 4. Examples of the DNA encoding monomeric human CRP preferably include a DNA encoding an amino acid sequence comprising the sequence represented by SEQ ID NO: 7, more preferably a DNA comprising the nucleotide sequence represented by SEQ ID NO: 9.

The DNA encoding an amino acid sequence comprising the sequence represented by SEQ ID NO: 1 or 7 encompasses a DNA encoding an amino acid sequence that is derived from this amino acid sequence by at least one mutation selected from the deletion, substitution, addition, and insertion of one or more amino acids and has predetermined homology to this sequence as long as these amino acid sequences are functionally equivalent. In this context, examples of the predetermined homology include 60% or higher homology, preferably 70% or higher homology, more preferably 80% or higher homology, further preferably 90% or higher homology.

The nucleotide sequence represented by SEQ ID NO: 4 or 9 encompasses a nucleotide sequence that is derived from this nucleotide sequence by at least one mutation selected from the deletion, substitution, addition, and insertion of one or more bases and has predetermined homology to this sequence as long as proteins encoded by these nucleotide sequences are functionally equivalent. In this context, examples of the predetermined homology include 60% or higher homology, preferably 70% or higher homology, more preferably 80% or higher homology, further preferably 90% or higher homology.

The amino acid sequence of monomeric canine CRP represented by SEQ ID NO: 1 has 60% sequence homology to the amino acid sequence of monomeric human CRP represented by SEQ ID NO: 7. The nucleotide sequence of monomeric canine CRP represented by SEQ ID NO: 4 has 60% sequence homology to the nucleotide sequence of monomeric human CRP represented by SEQ ID NO: 9.

In this context, the sequence homology can be calculated by pairwise alignment under default conditions using CLUSTALW2 tool provided by EBI.

In the present specification, the term "functionally equivalent" means that a protein or a polypeptide consisting of an unmutated amino acid sequence and a protein or a polypeptide consisting of a mutated amino acid sequence have similar biological or biochemical activity. In this context, the similar biological or biochemical activity specifically means that the protein or the polypeptide consisting of a mutated amino acid sequence can function as in serum-derived CRP and be used as a calibrator for CRP assay kits used in the field of clinical study and as an antigen for CRP assay kits in preparing anti-CRP antibodies.

The monomeric CRP-encoding DNA commonly used in the present invention is more preferably a DNA encoding monomeric CRP having a signal peptide. This is because the presence of the signal peptide promotes the secretion of pentameric CRP produced by the method of the present invention for producing pentameric CRP and facilitates the collection of this pentameric CRP.

The signal peptide is amino acid residues required for a secretory protein to pass through the lipid bilayer after being synthesized on the endoplasmic reticulum-bound ribosome. In general, the secretory protein is finally synthesized in the form of a mature active protein with the signal peptide N-terminally linked thereto. This signal peptide is removed after secretion.

Examples of the signal peptide-encoding DNA that can be used in the present invention can include DNAs encoding signal peptides derived from humans, dogs, mice, rats, rabbits, donkeys, goats, horses, birds, cats, enzymes, and insects. Among them, a DNA encoding a signal peptide derived from canine CRP or a signal peptide derived from an insect is preferable for producing canine CRP. Alternatively, a DNA encoding a signal peptide derived from human CRP or a signal peptide derived from an insect is preferable for producing human CRP.

In this context, examples of the DNA encoding a signal peptide derived from canine CRP preferably include a DNA encoding an amino acid sequence comprising the sequence represented by SEQ ID NO: 2, more preferably a DNA comprising the nucleotide sequence represented by SEQ ID NO: 5. Examples of the DNA encoding a signal peptide derived from human CRP preferably include a DNA encoding an amino acid sequence comprising the sequence represented by SEQ ID NO: 8, more preferably a DNA comprising the nucleotide sequence represented by SEQ ID NO: 10.

The DNA encoding monomeric CRP having a signal peptide that can be used in the present invention is a DNA in which the signal peptide-encoding DNA that can be used in the present invention is linked to the 5' end of the above-described monomeric CRP-encoding DNA commonly used in the present invention.

In this context, examples of the DNA encoding monomeric CRP having a signal peptide preferably include a DNA encoding an amino acid sequence comprising the sequence represented by SEQ ID NO: 3, more preferably a DNA comprising the nucleotide sequence represented by SEQ ID NO: 6.

The DNA encoding an amino acid sequence comprising the sequence represented by SEQ ID NO: 3 encompasses a DNA encoding an amino acid sequence that is derived from this amino acid sequence by at least one mutation selected from the deletion, substitution, addition, and insertion of one or more amino acids and has predetermined homology to this sequence as long as these amino acid sequences are functionally equivalent. In this context, examples of the predetermined homology include 60% or higher homology, preferably 70% or higher homology, more preferably 80% or higher homology, further preferably 90% or higher homology.

The nucleotide sequence represented by SEQ ID NO: 6 encompasses a nucleotide sequence that is derived from this nucleotide sequence by at least one mutation selected from the deletion, substitution, addition, and insertion of one or more bases and has predetermined homology to this sequence as long as proteins encoded by these nucleotide sequences are functionally equivalent. In this context, examples of the predetermined homology include 60% or higher homology, preferably 70% or higher homology, more preferably 80% or higher homology, further preferably 90% or higher homology.

The preparation step of the method of the present invention for producing pentameric CRP or the introduction step of the method of the present invention for producing a transgenic silkworm involves introducing a transgene DNA comprising the above-described monomeric CRP-encoding DNA commonly used in the present invention into a silkworm to be transformed, to prepare a transgenic silkworm.

In this context, the transgene DNA used in the preparation step of the method of the present invention for producing pentameric CRP or the introduction step of the method of the present invention for producing a transgenic silkworm needs only to have the monomeric CRP-encoding DNA commonly used in the present invention. Preferably, the transgene DNA comprises the monomeric CRP-encoding DNA whose expression is controlled directly or indirectly by a promoter of a DNA encoding a protein specifically expressed in a silkworm-derived silk gland, more preferably comprises: a transcription factor-encoding DNA operably linked downstream of a promoter of a DNA encoding a protein specifically expressed in a silkworm-derived silk gland; and the monomeric CRP-encoding DNA operably linked downstream of a target promoter of the transcription factor. This is because use of the promoter of a DNA encoding a protein specifically expressed in a silkworm-derived silk gland can facilitate the collection and purification of the pentamer and achieve the highly efficient production of the pentameric CRP, because the pentameric CRP is expressed in the silk gland, which is an organ that permits high-density protein expression in a confined space with few foreign proteins. In addition, the production efficiency of the protein from the transgene DNA can be improved depending on the selected combination between a transcription factor encoded by the DNA operably linked to this promoter and a target promoter of the transcription factor.

The phrase "expression is controlled directly or indirectly by a promoter" described for DNA expression means that the DNA of interest is operably linked downstream of the promoter or the transcription factor-encoding DNA is operably linked downstream of the promoter such that the expression of the DNA of interest is induced by this transcription factor.

The promoter of a DNA encoding a protein specifically expressed in a silkworm-derived silk gland can be any promoter that effectively functions in silkworm cells. The promoter is preferably a promoter devised to induce protein expression specific for the silk gland of the silkworm. Examples thereof include a promoter of a DNA encoding any of fibroin L-chain protein, fibroin H-chain protein, p25 protein, a protein synthesized from sericin 1 gene, and a protein synthesized from sericin II gene.

Examples of the combination between the transcription factor encoded by the DNA operably linked downstream of the promoter of a DNA encoding a protein specifically expressed in a silkworm-derived silk gland and its target promoter include the combination between a transcription factor GAL4 and a UAS sequence and the combination between a transcription factor TetR and a TRE sequence. Among them, the combination between GAL4 and UAS is preferable. This is because use of a GAL4/UAS system (Fischer, J. A. et al., Nature, 332, 853-856, 1988; and Brand, A. H. & Perrimon, N., Development, 118, 401-415, 1993) using GAL4 and UAS can accurately control the expression site, time, and level of the gene of interest and facilitate its expression in many tissues. Also, a strain may be prepared even using a lethal gene to be expressed.

According to a preferable aspect, examples of the transgene DNA used in the present invention include a DNA comprising: a GAL4-encoding DNA linked downstream of a promoter of a DNA encoding a protein synthesized from the sericin I gene; and the above-described DNA encoding monomeric CRP having a signal peptide, the DNA being linked downstream of the UAS sequence.

The silkworm to be transformed in the preparation step of the method of the present invention for producing pentameric CRP or the introduction step of the method of the present invention for producing a transgenic silkworm is not particularly limited and is preferably a silkworm having the suppressed production of a silk-constituting protein such as fibroin protein due to a mutation in a DNA region (including a coding region, a promoter region, and a noncoding region) encoding the silk-constituting protein, for producing pentameric CRP with high efficiency Examples of such a silkworm include silkworm mutants having the suppressed production of the silk-constituting protein, preferably naked pupa strains of silkworms having the suppressed production of the silk-constituting protein due to the mutation, Any silkworm having the suppressed production of the silk-constituting protein may be used in the present invention, regardless of whether or not the suppressed production of the silk-constituting protein is artificially caused or depends on a mutation occurring in the natural world.

Alternatively, a silkworm having the property of delivering non-diapause eggs or a silkworm having the property of delivering diapause eggs (e.g., commercial varieties Gunma 200, Shunrei, Shogetsu, Kinshu, or Showa) can be used as the silkworm to be transformed. In this context, the diapause eggs refer to eggs whose embryogenesis is temporarily halted after spawning, while the non-diapause eggs refer to eggs that hatch into larvae without such a halt in embryogenesis after spawning.

A DNA introduction method for introducing the transgene DNA into the silkworm to be transformed in the preparation step of the method of the present invention for producing pentameric CRP or the introduction step of the method of the present invention for producing a transgenic silkworm is not particularly limited as long as the method achieves the stable chromosomal integration of the transgene DNA in the silkworm to be transformed. The method that can be used involves, for example, constructing a recombinant vector comprising the transgene DNA and microinjecting this recombinant vector into a silkworm egg (Tamura, T. et al., Nat. Biotechnol., 18, 81-84, 2000), or employs a gene gun. Among others, a preferable method involves microinjecting, into a silkworm egg, a helper vector comprising a DNA encoding transposase, simultaneously with a recombinant vector containing the DNA to be introduced into silkworm according to the present invention between the terminal inverted repeats of transposon (Tamura, T. et al., Nat. Biotechnol., 18, 81-84, 2000).

Examples of the helper vector include, but not limited to, pHA3PIG (Tamura, T. et al., Nat. Biotechnol., 18, 81-84, 2000).

The transposon is preferably, but not limited to, piggyBac. Alternatively, mariner, minos, or the like may be used.

The transgene DNA may be divided and used in the introduction into the silkworm to be transformed. Examples of such an approach include: a method involving introducing a half of the DNA into a silkworm and artificially introducing the other half into an egg spawned by the resulting silkworm in the same way as above; and a method involving introducing the both halves of the DNA into one egg.

Alternatively, the preparation step of the method of the present invention for producing pentameric CRP or the introduction step of the method of the present invention for producing a transgenic silkworm may involve dividing the transgene DNA into pieces and introducing respective pieces into the different silkworms to be transformed, and subsequently mating the resulting transgenic adult silkworms containing the DNAs different from each other to prepare a transgenic silkworm containing the whole transgene DNA.

Preferably, the transcription factor-encoding DNA operably linked downstream of a promoter of a DNA encoding a protein specifically expressed in a silkworm-derived silk gland in the transgene DNA is introduced into the silkworm to be transformed, according to the above-described DNA introduction method. Subsequently, the monomeric CRP-encoding DNA (commonly used in the present invention) operably linked downstream of a target promoter of the transcription factor in the transgene DNA is introduced into another silkworm to be transformed, according to the DNA introduction method. Finally, these two types of adult silkworms are mated to obtain a transgenic silkworm having the whole transgene DNA as a next-generation silkworm.

In this method, the transcription factor can be introduced in one silkworm to be transformed so that expression tissues, time, levels, etc. can be determined on the basis of this transcription factor. The resulting silkworm is mated with a strain containing the gene to be expressed. As a result, each tissue, time, level, etc. can be changed advantageously without the creation of many strains. Even when the transgenic silkworm becomes infertile due to the expression of the gene of interest, a strain can be prepared. Tn addition, the amount of products from the transgene DNA can be increased depending on the selected transcription factor.

According to a preferable aspect of the transgenic silkworm preparation of the present invention, a silkworm containing a GAL4-encoding DNA linked downstream of a promoter of a DNA encoding a protein synthesized from the sericin I gene is mated with a silkworm containing a DNA comprising the monomeric CRP (having a signal peptide)-encoding DNA linked downstream of the UAS sequence to prepare a transgenic silkworm.

The transgenic silkworm prepared in the preparation step of the method of the present invention for producing pentameric CRP is a silkworm that has the stable chromosomal integration of the transgene DNA comprising the monomeric CRP-encoding DNA and produces pentameric CRP. The transgenic silkworm is preferably a silkworm that expresses and secretes pentameric CRP. In this context, the secretion of pentameric CRP by the transgenic silkworm facilitates the collection of the pentameric CRP from the silkworm.

According to a more preferable aspect, the transgenic silkworm used in the method of the present invention for producing pentameric CRP produces pentameric CRP into its silk gland. According to a particularly preferable aspect, the transgenic silkworm produces pentameric CRP by expressing and secreting the pentameric CRP into its silk gland. This is because this approach can facilitate the collection and purification of the pentameric CRP and achieve the highly efficient production of the pentameric CRP, because the pentameric CRP is produced and secreted into the silk gland, which is an organ that permits high-density protein expression in a confined space with few foreign proteins.

The collection step of the method of the present invention for producing pentameric CRP is the step of collecting and purifying pentameric CRP produced by the transgenic silkworm, preferably pentameric CRP produced by expression and secretion from the transgenic silkworm, to produce the pentameric CRP of interest.

Examples of the method for collecting pentameric CRP produced by the transgenic silkworm in the collection step of the method of the present invention for producing pentameric CRP include a method involving extracting the pentameric CRP from pentameric CRP-containing secretions. In this context, examples of the secretions include liquid silk or silk threads secreted by the silk gland, and fat body secretions. Particularly, liquid silk or silk threads secreted from a middle or posterior silk gland are preferable because of the large amount of the secretions. Liquid silk is more preferable because of easy collection.

Examples of the method for collecting the liquid silk from the silk gland include a method involving: dissecting the silkworm at the spinning stage; excising the silk gland therefrom; then making a small cut in the silk gland with tweezers or a scalpel in a buffer solution or placing the silk gland in a buffer solution, which is then stirred with a vortex mixer; and collecting liquid silk released into the buffer solution. In addition, examples of the method for collecting the silk threads can include a method involving collecting silk threads from cocoon spun by the transgenic silkworm, a method using a surfactant, and other methods generally known by those skilled in the art involving, for example, dissolution in an aqueous solution.

Examples of the method for collecting the secretions from the fat body can include a method involving excising the fat body from larvae, making a small cut in the fat body with tweezers or a scalpel in a buffer solution, and collecting the secretions released into the buffer solution, and other methods generally known by those skilled in the involving, for example, releasing the secretions from the fat body into a body fluid and collecting the body fluid.

According to a preferable aspect, examples of the method for collecting the pentameric CRP-containing secretions in the present invention include a method involving dissecting the silkworm at the spinning stage, excising the silk gland therefrom, and then extracting liquid silk in a buffer solution, followed by collection. This method facilitates the purification of pentameric CRP after the collection of liquid silk.

In the collection step of the method of the present invention for producing pentameric CRP, the pentameric CRP contained in the secretions can be purified by, for example, gel filtration chromatography, affinity chromatography, cation-exchange chromatography, anion-exchange chromatography, or combination thereof. Among them, affinity chromatography is preferable because the pentameric CRP can be purified easily. The affinity chromatography preferably employs a phosphoryl choline column, because the pentameric CRP can be purified with its structure maintained without being denatured.

The reactivity of the pentameric CRP produced by the method of the present invention for producing pentameric CRP can be evaluated by ELISA generally known by those skilled in the art. This ELISA method can employ anti-CRP antibodies known in the art.

The pentameric CRP produced by the method of the present invention for producing pentameric CRP exhibits concentration-dependent reactivity, as in serum-derived CRP, in the reactivity evaluation by ELISA, though this will be described later in detail in Examples. Thus, the pentameric CRP produced by the method of the present invention for producing pentameric CRP may be used instead of serum-derived CRP in CRP assay kits, etc.

The transgenic silkworm provided by the present invention is a silkworm that has the stable chromosomal integration of the transgene DNA comprising the monomeric CRP-encoding DNA and produces pentameric CRP. The transgenic silkworm is preferably a silkworm that expresses and secretes pentameric CRP. In this context, the secretion of pentameric CRP by the transgenic silkworm facilitates the collection of the pentameric CRP from the silkworm.

According to a more preferable aspect, the transgenic silkworm provided by the present invention produces pentameric CRP into its silk gland. According to a particularly preferable aspect, the transgenic silkworm produces pentameric CRP by expressing and secreting the pentameric CRP into its silk gland. This is because this approach can facilitate the collection and purification of the pentameric CRP and achieve the highly efficient production of the pentameric CRP, because the pentameric CRP is produced and secreted into the silk gland, which is an organ that permits high-density protein expression in a confined space with few foreign proteins.

The transgenic silkworm provided by the present invention or the transgenic silkworm prepared in the preparation step of the method of the present invention for producing pentameric CRP is allowed to express pentameric CRP, which is not possessed by natural silkworms. Nevertheless, this transgenic silkworm can be passaged in the same way as in usual silkworms. In addition, offspring silkworms can produce pentameric CRP.

For example, eggs are incubated under usual conditions, and newly hatched larvae can be brushed off to artificial feed or the like and raised into fifth instar larvae under the same conditions as in usual silkworms.

The transgenic silkworm provided by the present invention or the transgenic silkworm used in the method of the present invention for producing pentameric CRP pupates as in usual silkworms. Pupae are sexually divided, and male and female silkworm moths are mated, followed by egg removal on the next day. The silkworm eggs can be stored as in usual silkworm eggs. The transgenic silkworm provided by the present invention or the transgenic silkworm used in the method of the present invention for producing pentameric CRP can be passaged by repetitively performing such raising.

The transgenic silkworm obtained by this passage can be raised in a clean environment with artificial feed and can be raised easily at a large scale of the order of several ten thousands. In addition, the silkworm can be raised at a large scale using mulberry leaves abundant in the natural world to inexpensively obtain pentameric CRP in large amounts.

Specifically, the large-scale raised transgenic silkworm provided by the present invention or transgenic silkworm used in the method of the present invention for producing pentameric CRP can be used to produce pentameric CRP with high efficiency.

The method of the present invention for producing a transgenic silkworm is a method for producing a transgenic silkworm producing pentameric CRP through the introduction step and is preferably a method for producing a transgenic silkworm that expresses and secretes pentameric CRP.

According to a more preferable aspect, the method of the present invention for producing a transgenic silkworm is a method for producing a transgenic silkworm that produces pentameric CRP into its silk gland. According to a particularly preferable aspect, the method of the present invention for producing a transgenic silkworm is a method for producing a transgenic silkworm that expresses and secretes pentameric CRP into its silk gland.

The monomeric canine CRP-encoding DNA provided by the present invention is a DNA having a nucleotide sequence encoding an amino acid sequence comprising the sequence represented by SEQ ID NO: 1, preferably a DNA having the nucleotide sequence represented by SEQ ID NO: 4.

According to a more preferable aspect, the monomeric canine CRP-encoding DNA provided by the present invention is a DNA encoding monomeric canine CRP having a signal peptide. Examples of the DNA encoding monomeric canine CRP having a signal peptide include a DNA having a nucleotide sequence encoding an amino acid sequence having the sequence represented by SEQ ID NO: 3, preferably a DNA having the nucleotide sequence represented by SEQ ID NO: 6.

The DNA encoding an amino acid sequence comprising the sequence represented by SEQ ID NO: 1 or 3 encompasses a DNA encoding an amino acid sequence that is derived from this amino acid sequence by at least one mutation selected from the deletion, substitution, addition, and insertion of one or more amino acids and has predetermined homology to this sequence as long as these amino acid sequences are functionally equivalent. In this context, examples of the predetermined homology include 60% or higher homology, preferably 70% or higher homology, more preferably 80% or higher homology, further preferably 90% or higher homology.

The nucleotide sequence represented by SEQ ID NO: 4 or 6 encompasses a nucleotide sequence that is derived from this nucleotide sequence by at least one mutation selected from the deletion, substitution, addition, and insertion of one or more bases and has predetermined homology to this sequence as long as proteins encoded by these nucleotide sequences are functionally equivalent. In this context, examples of the predetermined homology include 60% or higher homology, preferably 70% or higher homology, more preferably 80% or higher homology, further preferably 90% or higher homology.

A host that permits pentameric CRP production can be transformed with the monomeric canine CRP-encoding DNA provided by the present invention to produce, in a genetic engineering manner, pentameric canine CRP having activity as described later in detail in Examples.

The expression vector provided by the present invention is an expression vector comprising the monomeric canine CRP-encoding DNA and is preferably an expression vector in which the monomeric canine CRP-encoding DNA is operably linked downstream of UAS. In this context, an expression vector comprising the monomeric canine CRP-encoding DNA operably linked downstream of UAS is introduced into a host having a GAL4-encoding DNA operably linked downstream of a promoter of a DNA encoding a protein expressed in a site-specific manner. As a result, the expression site, time, and level of CRP can be controlled accurately.

Examples of a vector on which the expression vector provided by the present invention is based include M13, pUC, pBac, pBP322, pBluescript, and pCR-Script vectors, but are not particularly limited thereto.

The expression vector provided by the present invention can be used for introducing the monomeric canine CRP-encoding DNA into the silkworm to be transformed, in the preparation step of the method of the present invention for producing pentameric CRP or the introduction step of the method of the present invention for producing a transgenic silkworm and can also be used in the DNA introduction of hosts other than silkworms.

The introduction of the expression vector into the host can be carried out by a method generally known by those skilled in the art, for example, electroporation.

The expression vector provided by the present invention can be introduced into a host that permits pentameric CRP production to produce, in a genetic engineering manner, pentameric canine CRP having activity as described later in detail in Examples.

Hereinafter, the present invention will be described more specifically with reference to Examples. However, the present invention is not limited to these Examples by any means.

EXAMPLE 1

As described in detail below, a silkworm containing a DNA that encoded a monomeric canine CRP having a signal peptide and was linked downstream of a UAS sequence was mated with a silkworm containing a GAL4-encoding DNA linked downstream of a promoter of a DNA encoding a protein synthesized from the sericin I gene to prepare a transgenic silkworm. Canine CRP produced by the transgenic silkworm into its silk gland was collected and examined for its physical properties.

(1) Construction of Plasmid Vector pBac-UAS-cfCRP-SV40

A plasmid vector comprising a UAS sequence and its downstream-linked DNA (cfCRP) encoding monomeric canine CRP having a signal peptide was constructed. Specifically, a nucleotide sequence corresponding to a mature region in the canine CRP gene was determined, and a plasmid vector comprising this nucleotide sequence was constructed as shown in FIG. 1. The nucleotide sequence of the canine CRP gene was referred to the predicted sequence of canine CRP (NCBI Reference Sequence: XM_545746).

More specifically, homology search was conducted between an amino acid sequence obtained by the translation of the predicted nucleotide sequence of the canine CRP gene and the amino acid sequences of mature forms of CRPs derived from various animals (humans, mice, rabbits, pigs, and cattle) having the identified amino acid sequences. A highly homologous region was regarded as a mature region. This mature region refers to a portion presumed to become a CRP monomer and has the nucleotide sequence of SEQ ID NO: 4. Its molecular weight was presumed to be 22.9 kDa from the amino acid sequence. Likewise, homology search was conducted using the amino acid sequences of the signal peptides of various animal CRPs. A highly homologous region was regarded as a signal peptide having the nucleotide sequence of SEQ ID NO: 5.

Subsequently, a nucleotide sequence (cfCRP) having the nucleotide sequence of SEQ ID NO: 6 was designed so that a signal peptide-encoding nucleotide sequence having the nucleotide sequence of SEQ ID NO: 5 was added to the 5' end of the nucleotide sequence of SEQ ID NO: 4 corresponding to the mature region. After total synthesis of the designed nucleotide sequence, the synthesized DNA was inserted to a pUC57 plasmid to construct a pUC57-cfCRP plasmid. Restriction sites (SpeI) were disposed at both ends of cfCRP ORF.

Subsequently, the pUC57-cfCRP plasmid was treated with SpeI to obtain a cfCRP fragment. Finally, the cfCRP fragment was inserted to the BlnI site of pBac-UAS-SV40 to construct a plasmid vector pBac-UAS-cfCRP-SV40 (FIG. 1) for preparing a transgenic silkworm.

(2) Preparation of Transgenic Silkworm Producing Canine CRP

The plasmid vector pBac-UAS-cfCRP-SV40 constructed in the preceding step (1) was introduced into a silkworm. Also, a promoter (Ser1) of a DNA encoding a protein synthesized from the sericin I gene and its downstream-linked GAL4-encoding DNA (GAL4) were introduced into a silkworm. The silkworms thus prepared were mated to prepare a transgenic silkworm producing canine CRP.

Specifically, pBac-UAS-cfCRP-SV40 constructed in the preceding step (1) and a helper plasmid pA3PIG (Tamura, T. et al., Nat. Biotechnol., 18, p. 81-84, 2000) encoding the transposase gene were microinjected to each of 433 silkworm eggs at the early development stage. In this context, the gene introduction was performed according to a polynucleotide introduction method described in JP 2003-88273 A.

Subsequently, the first-generation silkworms hatched from the transgenic silkworm eggs were mated. The resulting second-generation larvae were examined for the expression of KMO marker genes on their body surfaces.

Eight larvae expressing the KMO marker genes were identified from one out of 62 mated batches. These individuals were passaged to establish silkworm strains each having the canine CRP gene.

Subsequently, these canine CRP strains of the silkworms were mated with the already-established silkworm strain Ser1GAL4 (Toshiki Tamura, et al., Abstracts of the Meeting of the Japanese Society of Sericultural Science, 74, p. 51, 2004) containing a promoter (Ser1) of a DNA encoding a protein synthesized from the sericin I gene and its downstream-linked GAL4-encoding DNA (GAL4). An individual coexpressing the KMO marker gene possessed by the canine CRP strain and the DsRed marker gene possessed by the Ser1GAL4 strain was selected from among the next-generation silkworms obtained by this mating.

(3) Extraction of Canine CRP

Canine CRP was extracted from the larvae at the spinning stage of the transgenic silkworms selected in the preceding step (2). Its reactivity was confirmed.

Specifically, canine CRP from the silk glands of the prepared canine CRP-producing transgenic silkworms was extracted into a buffer solution (50 mM Tris-HCl (pH 7.4), 150 mM NaCl, 10 mM CaCl2) and centrifuged at 24000 rpm at 4° C. for 15 min. The resulting supernatant was collected.

The obtained supernatant was confirmed by a canine CRP ELISA assay kit (manufactured by Immunology Consultants Laboratory, Inc.) to contain canine CRP. Also, the supernatant was serially diluted, and canine CRP levels in the diluted solutions were determined to confirm dilution linearity (FIG. 2).

Figure 2:
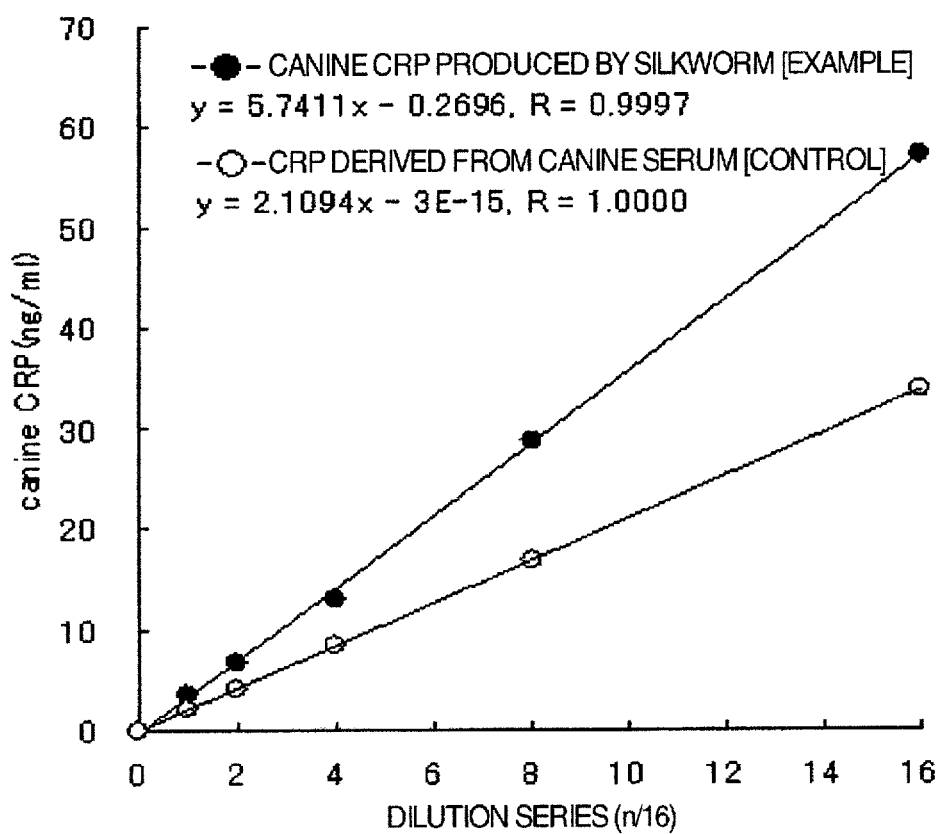
FIG. 2 is a diagram showing the dilution linearity of assay on the dilution series of canine CRP produced by a silkworm obtained by the production method of the present invention and the dilution series of canine serum-derived CRP as a control using a canine CRP ELISA assay kit. The abscissa represents the concentration (n/16, 0≤n≤16) of a diluted solution when the concentration of an undiluted solution is defined as 1. The ordinate represents a CRP concentration (ng/ml). The filled circle represents the dilution linearity of canine CRP produced by a silkworm. The open circle represents the dilution linearity of canine serum-derived CRP.

Canine serum was serially diluted as a control, and canine CRP levels in the diluted solutions were determined using a canine CRP ELISA assay kit (manufactured by Immunology Consultants Laboratory, Inc.) to confirm dilution linearity (FIG. 2).

The results demonstrated that the recombinant canine CRP obtained from the canine CRP-producing transgenic silkworm had reactivity equivalent to canine serum-derived CRP.

(4) Purification of Canine CRP

Canine CRP was separated and purified from the canine CRP solution extracted from the canine CRP-producing transgenic silkworm in the preceding step (3).

Specifically, the canine CRP extracts were filtered through a 0.45-µm filter to prepare a purification sample. This purification sample was applied to Immobilized p-Aminophenyl Phosphoryl Choline column (manufactured by Thermo Scientific Pierce; 1 ml). This column was equilibrated in advance with 50 mM Tris-HCl (pH 7.4), 150 mM NaCl, and 10 mM CaCl2.

Subsequently, the column was washed with 20 ml of 50 mM Tris-HCl (pH 7.4), 2 M NaCl, and 10 mM CaCl2. Then, 50 mM Tris-HCl (pH 7.4), 150 mM NaCl, and 10 mM phosphoryl choline were applied to the column to elute canine CRP.

A rise in absorbance was confirmed in the obtained canine CRP fraction using a canine CRP ELISA assay kit (manufactured by Immunology Consultants Laboratory, Inc.) (Table 1).

TABLE 1

Assay results of purified canine CRP using canine CRP ELISA assay kit

| | Absorbance (OD) |
|---|---|
| Saline | 0.058 |
| Purified canine CRP | 0.588 |

(5) Molecular Weight Analysis on Canine CRP

The molecular weight of the canine CRP purified in the preceding step (4) was measured.

Figure 3:
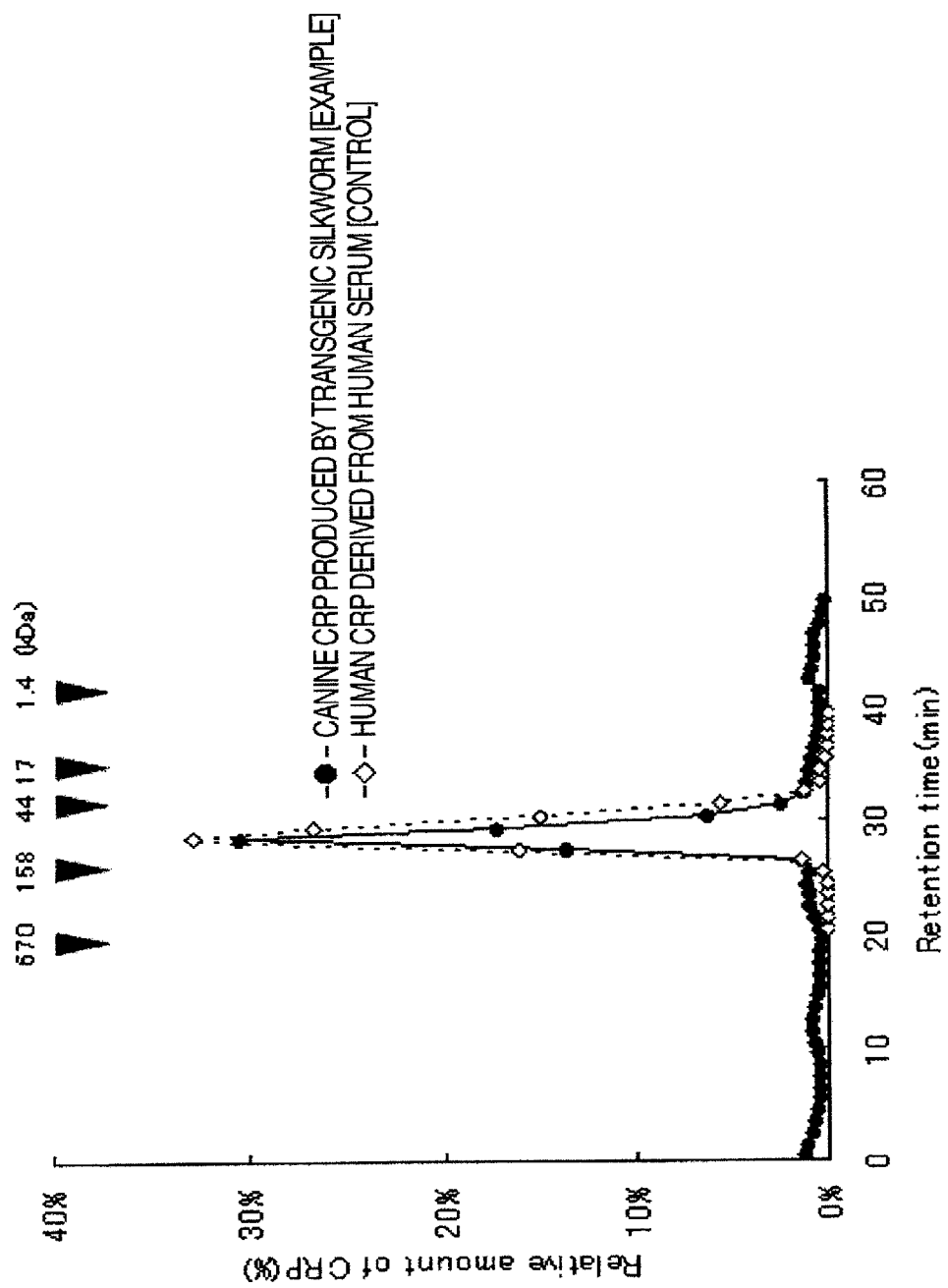
FIG. 3 is a diagram showing results of subjecting canine CRP produced by a silkworm obtained by the production method of the present invention and human serum-derived CRP as a control to Superdex 200 gel filtration chromatography. The abscissa represents a retention time (min). The ordinate represents canine CRP or human CRP levels contained in each elution fraction (ratio to CRP levels contained in all elution fractions; % by weight). The filled circle and the solid line represent the results of gel filtration chromatography about canine CRP produced by a silkworm. The open rhombus and the broken line represent the results of gel filtration chromatography about human serum-derived CRP.

Specifically, the purified canine CRP solution was used as a sample for gel filtration chromatography. This sample was applied to a Superdex 200 gel filtration chromatography column (FIG. 3). This column was equilibrated in advance with 50 mM Tris-HCl (pH 8.0) and 0.5 M NaCl. Also, CRP levels in each elution fraction were determined using a canine CRP ELISA assay kit (manufactured by Immunology Consultants Laboratory, Inc.).

Molecular weight markers thyroglobulin (M.W. 670 kDa), r-globulin (M.W. 158 kDa), ovalbumin (M.W. 44 kDa), myoglobin (M.W. 17 kDa), and vitamin B12 (M.W. 1.35 kDa) were applied to the column under the same conditions as above, and their retention times were compared with that of the canine CRP to determine the molecular weight of the canine CRP.

Human CRP derived from human serum was applied to the column as a control under the same conditions as above, and its retention time was compared with that of the canine CRP (FIG. 3). CRP levels in each elution fraction were determined using LA CRP-S(D) (manufactured by Nittobo Medical Co., Ltd.).

In this context, the canine CRP monomer is presumed to have a molecular weight of 22.9 kDa, whereas the human CRP monomer has a molecular weight of 23.0 kDa and is present in a pentameric form in serum.

The results of comparison with the molecular weight markers demonstrated that the canine CRP had a molecular weight of approximately 100 kDa. The canine CRP produced by the transgenic silkworm was also confirmed to exhibit the same retention time as in human CRP derived from human serum. These molecular weight analysis results demonstrated that the canine CRP purified from the silkworm was in a pentameric form. Monomeric canine CRP was not contained in this purification fraction. Thus, pentameric canine CRP similar to those present in vivo was successfully obtained.

INDUSTRIAL APPLICABILITY

The method of the present invention for producing pentameric CRP can produce, with high efficiency, pentameric CRP having activity equivalent to serum-derived CRP. CRP produced by the method of the present invention for producing pentameric CRP can be used as a calibrator for CRP assay kits used in the field of clinical study. Also, CRP produced by the present invention can be used as an antigen for CRP assay kits in preparing anti-CRP antibodies.

Free Text for Sequence Listing

SEQ ID NO: 1—Amino acid sequence of canine CRP

SEQ ID NO: 2—Amino acid sequence of a signal peptide derived from canine CRP

SEQ ID NO: 3—Description of artificial sequence: Amino acid sequence comprising the amino acid sequence (SEQ ID NO: 1) of canine CRP linked to the amino acid sequence (SEQ ID NO: 2) of the signal peptide derived from canine CRP SEQ ID NO: 4—Nucleotide sequence of canine CRP SEQ ID NO: 5—Nucleotide sequence of a signal peptide derived from canine CRP SEQ ID NO. 6—Description of artificial sequence: Nucleotide sequence comprising the nucleotide sequence (SEQ ID NO: 4) of canine CRP linked to the nucleotide sequence (SEQ ID NO: 5) of the signal peptide derived from canine CRP SEQ ID NO: 7—Amino acid sequence of human CRP SEQ ID NO: 8—Amino acid sequence of a signal peptide derived from human CRP SEQ ID NO: 9—Nucleotide sequence of human CRP SEQ ID NO: 10—Nucleotide sequence of a signal peptide derived from human CRP

---

The invention claimed is:

1. An isolated nucleic acid sequence encoding canine monomeric C reactive protein (CRP), wherein said nucleic acid sequence encodes the amino acid sequence as set forth in SEQ ID NO: 1.

2. An isolated nucleic acid sequence encoding canine monomeric CRP, wherein the nucleic acid sequence is set forth over the entire length of the sequence set forth in SEQ ID NO: 4.

3. An expression vector comprising the isolated nucleic acid sequence of claim 1.

4. The expression vector of claim 3, wherein the isolated nucleic acid sequence is operably linked downstream of a UAS.

5. An expression vector comprising the isolated nucleic acid sequence of claim 2.

6. The expression vector of claim 5, wherein the isolated nucleic acid sequence is operably linked downstream of a UAS.

* * * * *